(«12») United States Patent
Kameda et al.

(10) Patent No.: US 11,814,751 B2
(45) Date of Patent: Nov. 14, 2023

(54) METHOD FOR PRODUCING LONG BAGWORM SILK THREADS AND PRODUCTION DEVICE THEREFOR

(71) Applicant: National Agriculture and Food Research Organization, Ibaraki (JP)

(72) Inventors: Tsunenori Kameda, Ibaraki (JP); Taiyo Yoshioka, Ibaraki (JP)

(73) Assignee: NATIONAL AGRICULTURE AND FOOD RESEARCH ORGANIZATION, Ibaraki (JP)

( * ) Notice: Subject to any disclaimer, the term of this patent is extended or adjusted under 35 U.S.C. 154(b) by 532 days.

(21) Appl. No.: 16/626,815

(22) PCT Filed: Jun. 29, 2017

(86) PCT No.: PCT/JP2017/023839
§ 371 (c)(1),
(2) Date: Dec. 26, 2019

(87) PCT Pub. No.: WO2019/003364
PCT Pub. Date: Jan. 3, 2019

(65) Prior Publication Data
US 2020/0157706 A1    May 21, 2020

(51) Int. Cl.
*D01B 7/00* (2006.01)
*A01K 67/04* (2006.01)
(Continued)

(52) U.S. Cl.
CPC ............ *D01B 7/00* (2013.01); *A01K 67/04* (2013.01); *D01B 3/00* (2013.01); *D01B 7/04* (2013.01)

(58) Field of Classification Search
CPC ... D01B 7/00; D01B 7/04; D01B 3/00; A01K 67/04; A01K 67/033
(Continued)

(56) References Cited

U.S. PATENT DOCUMENTS

| 6,412,261 B1* | 7/2002 | Welshans | D01B 7/00 57/3 |
| 2005/0206103 A1* | 9/2005 | Schmidt | B62B 5/049 280/33.992 |
| 2013/0281668 A1 | 10/2013 | Vollrath | |

FOREIGN PATENT DOCUMENTS

| CN | 1139681 C * | 2/2004 | D02G 3/02 |
| CN | 103476790 A | 12/2013 | |

(Continued)

OTHER PUBLICATIONS

UNL Extension in Lancaster County, Nebraska. "Bagworm Control—UNL Extension in Lancaster County". Retrieved from Internet: https://www.youtube.com/watch?v=rtq3T0besEE (Year: 2009).*
(Continued)

*Primary Examiner* — Aiying Zhao
(74) *Attorney, Agent, or Firm* — Lucas & Mercanti, LLP

(57) ABSTRACT

Provided is a method of producing a long bagworm silk thread, the method comprising a spinning process of making a bagworm having its nest hang its legs on a rail and continuously spin a silk thread along the rail, wherein the rail has a width smaller than the maximum width between the left and right legs when the bagworm used spreads out its legs and wherein the rail is such that the bagworm can hang its legs on the rail, and a collection process of collecting a long silk thread from the rail after the spinning process.

6 Claims, 13 Drawing Sheets

(51) Int. Cl.
*D01B 3/00* (2006.01)
*D01B 7/04* (2006.01)

(58) Field of Classification Search
USPC .............................................................. 19/3
See application file for complete search history.

(56) References Cited

FOREIGN PATENT DOCUMENTS

| EP | 2210971 A1 * | 7/2010 | ........... A61L 27/227 |
|---|---|---|---|
| WO | WO-2005049899 A1 * | 6/2005 | ............... D01B 7/00 |
| WO | 2012/165477 A1 | 12/2012 | |

OTHER PUBLICATIONS

Reddy et al. "Structure and properties of ultrafine silk fibers produced by Theriodopteryx ephemeraeformis". Jul. 17, 2010. Journal of Materials Science. vol. 45, No. 24, pp. 6617-6622. (Year: 2010).*

Haibo,"What Happens in the Animal World", My Animal Friends, Yanbian University Press, 2013, pp. 146-150 English translation 5 pages.

Yoshioka et al., "A study of the extraordinarily strong and tough silk produced by bagworms", Nature Communications, 2019, vol. 10, No. 1469, pp. 1-11.

Office Action for Corresponding Chinese Application No. 201780092173.2, dated Jun. 28, 2021, 7 Pages.

Osaki, Shigeyoshi, "Animals Teach Science on Natural Fibers: Spider's Silks, Bagworm's Silks, and Collagen Fibers", Journal of the Society of Fiber Science and Technology, vol. 58, No. 3, 2002, and partial English translation of relevant portions (8 pages).

Kuwana, Yoshihiko; et al., "High-Toughness Silk Produced by a Transgenic Silkworm Expressing Spider (*Araneus ventricosus*) Dragline Silk Protein", PLoS ONE, vol. 9, No. 8: e105325. https://doi.org/10.1371/journal.pone.0105325, 2014 (11 pages).

Gosline, J.M.; et al., "The mechanical design of spider silks: from fibroin sequence to mechanical function", Journal of Experimental Biology, vol. 202, 1999, pp. 3295-3303.

Office Action for Corresponding Japanese Application No. 2019-526049, dated Aug. 31, 2021, 3 Pages.

"Hikari EB343-5 PVC Plate, White, 0.1x17.7 inches (3x300x450 mm)", Amazon Website, 5 pages, English Translation 6 pages.

"Aluminium Wire 150g 2.0 mm", Amazon Website, 8 pages, English Translation 7 pages.

Reddy, N; et al., "Structure and properties of ultrafine silk fibers produced by Theriodopteryx ephemeraeformis", J Mater Sci, 2010, vol. 45, pp. 6617-6622.

Howard, Lo; et al., "The bagworm. (*Thyridopteryx ephemeraeformis* Haw.): General Appearance and nature of attack", U.S. Dept. of Agriculture, Bureau of Entomology, 1908, Circular No. 97 (10 pages).

EPO, "The extended European search report", which was issued in connection with EP patent application No. EP17916093.2, and dated Feb. 24, 2021 (4 pages).

Haibo,"What Happens in the Animal World", My Animal Friends, University Press, 2013, pp. 146-150 English translation 5 pages.

* cited by examiner

Fig. 1
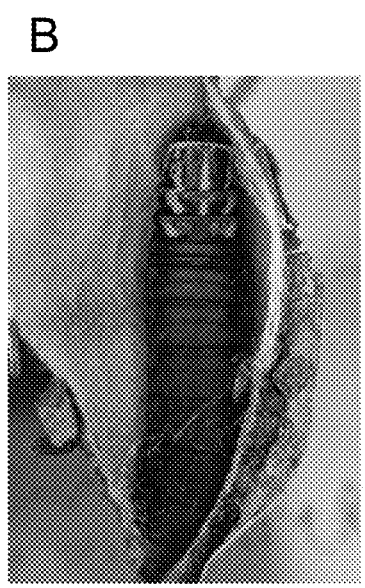

Fig. 2
A
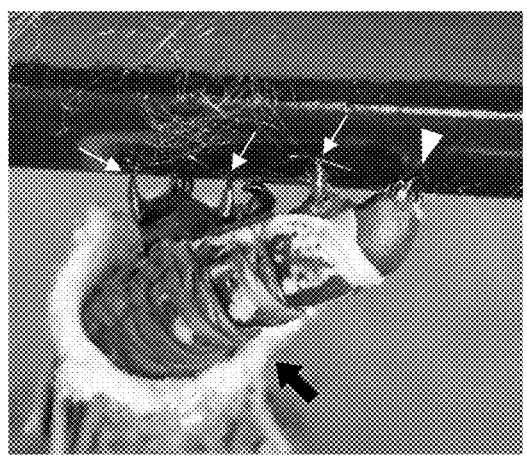
B
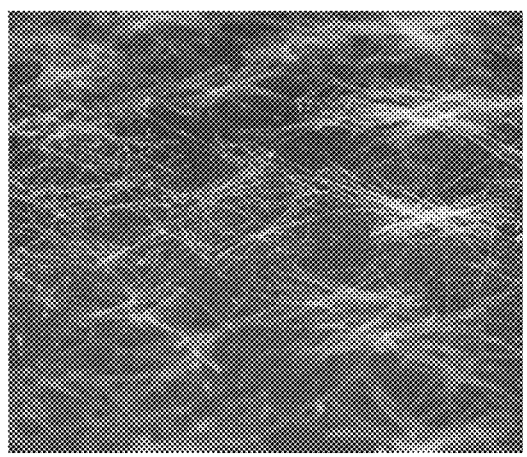

Fig. 3
A
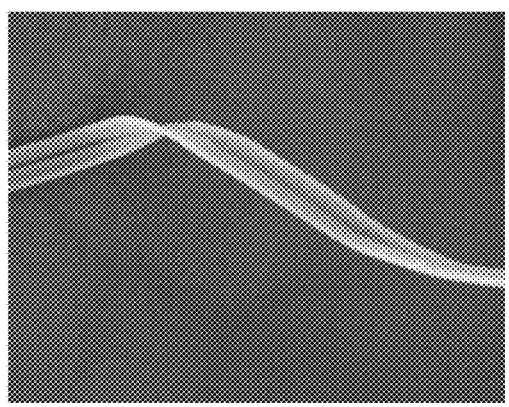
B
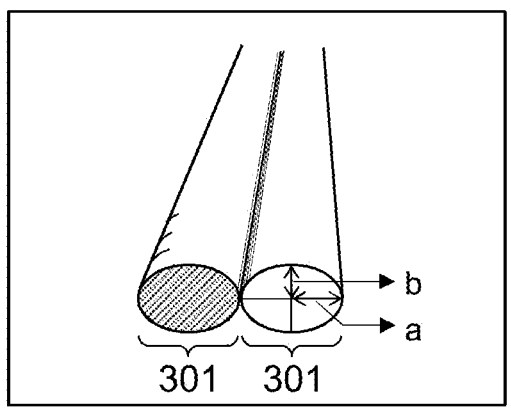

Fig. 6
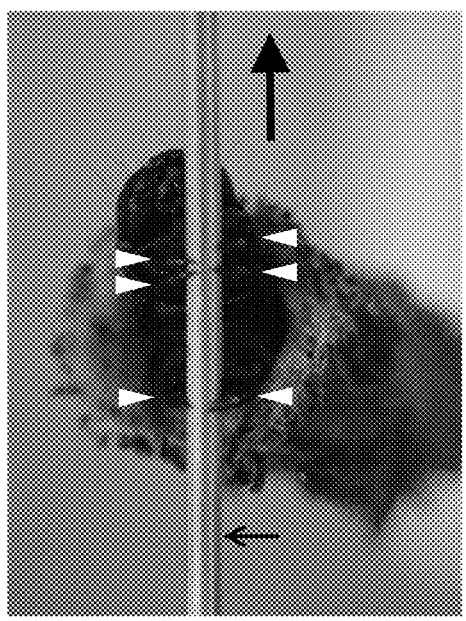
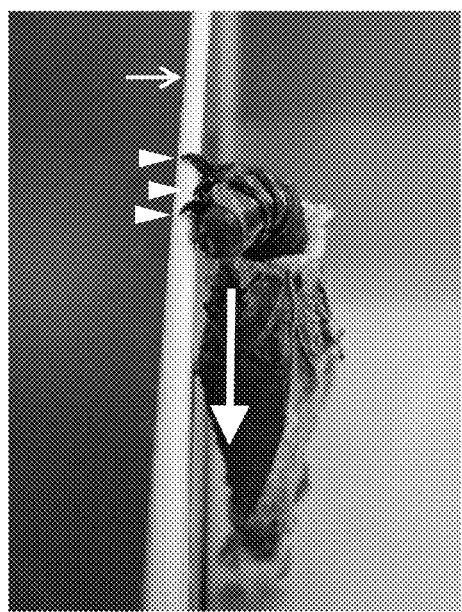

METHOD FOR PRODUCING LONG BAGWORM SILK THREADS AND PRODUCTION DEVICE THEREFOR

CROSS-REFERENCE TO RELATED APPLICATIONS

This application is a 371 of PCT/JP2017/023839, filed Jun. 29, 2017.

TECHNICAL FIELD

The present invention relates to a method of producing a long silk thread derived from a moth larva belonging to the family Psychidae, i.e, a bagworm, a device for producing the same and the like.

BACKGROUND ART

Threads consitituting insect cocoons and hairs of mammals have been used as animal fibers for clothes and the like since long time ago. Especially silk threads from a silk moth (Bombyx mori) larva, namely a silkworm, which are herein often referred to as "silkworm silk threads", have excellent properties for absorption and desorption of moisture, moisture retention, and heat retention, and also have a unique gloss and smooth texture. Therefore, the silkworm silk threads are valuable and expensive natural materials even today.

However, there exist animal fibers in nature having properties comparable or superior to those of silkworm silk threads. Recently, for utilizing animal fibers having such excellent properties as novel natural materials, exploration thereof and research thereon are ongoing.

Threads derived from spiders (herein often referred to as "spider thread") is one of such materials of interest. Spider threads have flexibility and elasticity and have an elastic force up to 5 to 6 times higher than that of polystyrene, and are thus expected as a medical material for surgical suture and the like, and as a special material for emergency ropes, protective clothes, or the like (Non-Patent Literatures 1 and 2). However, mass-production of spider threads is not possible because mass rearing of spiders and collecting a large amount of threads from spiders are difficult. Another problem is that the production cost is high. Currently, an attempt to overcome these problems is ongoing by using gene recombination technology to produce spider threads in silkworms or *Escherichia coli* (Patent Literature 1 and Non-Patent Literature 2). However, the silkworm or *Escherichia coli* used for spider thread production are recombinants and are thus allowed to be reared or cultured only in facilities having defined equipment, which disadvantageously involves a large maintenance or management burden. Additionally, spider thread proteins expressed in *Escherichia coli* are in a liquid state and are needed to be converted to fibers, which also disadvantageously increases the number of processes. Furthermore, another disadvantage is that currently spider threads spun by the recombinant silkworms are merely comprised in silkworm silk threads at several percentages and cannot be obtained as 100% spider threads which allow 100% of the properties of spider threads to be utilized.

There exist insects called bagworms (also known as "basket worms"). The larvae of moths belonging to the family Psychidae in the order Lepidoptera are collectively referred to as bagworms and are known to spend the whole larval stages living with spindle-shaped or cylinder-shaped nests (bag nests) made of pieces of leaves and twigs assembled by threads (FIG. 1), during which the larvae usually hide themselves inside the nests and move with the nests even for eating. Bagworms are also insects familiar to people from long time ago, and a bagworm with its nest hanging from a branch of a bare tree in winter time is a typical winter scene.

The bagworm-derived threads (herein often referred to as "bagworm silk threads") have mechanical properties superior to those of silkworm silk threads and spider threads. For example, bagworm silk threads from *Eumeta minuscula* have an elastic modulus up to 3.5 times of that of silkworm silk threads and 2.5 times of that of spider threads of Nephila clavata, and have a very high strength (Non-Patent Literatures 1 and 3). Additionally, a monofiber of bagworm silk threads has a cross-sectional area only about one-seventh of that of a monofiber of silkworm silk threads, which allows production of fine, thin and light fabrics with a smooth texture. Moreover, bagworm silk threads have a gloss and a shiny appearance comparable or superior to those of silkworm silk threads.

Bagworms are more advantageous than silkworms also in terms of rearing. For example, since silkworms feed on only raw leaves of mulberry (species belonging to the genus *Morus,* including, for example, *M. bombycis, M. alba,* and *M. Thou*) in principle, the region for rearing and season for rearing depend on the supply area of mulberry leaves and the season of mulberry leaf development. In contrast, bagworms are euryphagous, the specificity for food leaves is low, and many species of bagworms can feed on leaves of trees of various species. Accordingly, food leaves for bagworms are easily obtainable and bagworms can be raised in any region. Also, bagworms of some species can feed on leaves of evergreen trees. Thus, differently from mulberries, which are deciduous trees, it is possible to supply food leaves all year round. Moreover, bagworms are smaller in size than silkworms and require a rearing space equal to or less than that required for rearing silkworms, which makes mass rearing easy. Thus, the cost for rearing can significantly be reduced compared with that for rearing silkworms.

Also, bagworms are more advantageous than silkworms in terms of productivity. For example, silkworms spin a large amount of threads only during cocooning and all larvae perform cocooning in the same period. Thus, a disadvantage of silkworms is that thread collection periods overlap and labor periods concentrate thereon. In contrast, bagworms repeatedly spin silk threads for nest building or migration throughout larval stages. Thus, bagworms have an advantage in that labor periods can be dispersed by artificially adjusting the thread collection periods. Additionally, bagworm silk threads can be directly collected from wild-type bagworms, and thus it is not required to generate or maintain recombinants as is required in the case of production of spider threads.

As described above, bagworm silk threads have properties superior to conventional animal fibers and also have many advantages for their production, and thus can be a very promising novel natural material.

However, in the practical application of bagworm silk threads, there are several major problems which are unavoidable and difficult to solve. The most important problem is that long monofibers cannot be obtained from bagworms. In the case of silkworms, cocooning is carried out by continuous spinning, and a long fiber can thus be relatively easily obtained by cocoon scouring and reeling. In contrast, bagworms pupate in their nests where the bagworms spend their lives in the larval stage, and therefore do not perform cocooning behavior before pupation. Additionally, since a nest of a bagworm is extended as the bagworm grows from the first instar in principle, old and new silk threads are mixed together in the nest. In addition, a nest of a bagworm has an opening at one end of the longitudinal axis (FIG. 2A: thick arrow), out of which the bagworm exposes its head and a portion of its thorax for migration and eating, and an outlet for excretion at the other end for excretion of feces and the like. Since a bagworm nest always has two openings, silk threads are fragmented in the nest and are discontinuous. Thus, bagworm nests are by its nature assembled by relatively short silk threads entangled with each other, and long fibers cannot be obtained from the nests by conventional methods. Furthermore, bagworm nests are composed of three layers, i.e., the outermost, intermediate, and innermost layers, and the outermost and intermediate layers comprise a large amount of gummy material, which are difficult to completely remove even if scouring is repeated. By conventional technologies, spinning can be performed only from the innermost layer, which does not comprise gummy material, but the silk threads less than 50 cm long can be merely obtained from the innermost layer.

Further, a bagworm spins a foothold silk thread for preventing fall from a branch or the like in a zigzag pattern (arrowhead), as shown in FIG. 2A, and hooks its claws on the thread for migration (thin arrow). Though this type of threads may be used as bagworm silk threads, collection of the type of threads is difficult because the migration of a bagworm depends on the bagworm and is difficult to control. Additionally, spinning again at the same place after spinning there produces multiple crossovers and complicated entanglement of silk threads spun in a zigzag pattern as shown in FIG. 2B, and thus collection of silk threads is difficult.

For the reason as described above, it has been considered to be almost impossible to obtain meter-scale bagworm silk threads as monofibers by conventional technologies. Therefore, fabrics interwoven with bagworm silk threads have not been known so far. In fact, conventional products using bagworm silk threads, such as purses or sandals, are merely manufactured using unwoven fabrics, which are prepared by removing contaminants, such as pieces of leaves and twigs, from bagworm nests, expanding and then shaping, followed by patching together the resulting products in a patchwork manner.

For practical application of the bagworm silk thread, another important problem is that pieces of leaves and twigs and the like are inevitably attached on the surface of bagworm nests. These contaminants have to be completely removed for commercialization of bagworm silk threads. However, the removing work requires enormous labor and cost, thus resulting in increased production cost. Additionally, complete removal of the contaminants is difficult with existing technologies, which leads to low quality of final products due to contamination with a small amount of small pieces of leaves as well as light-brown staining of silk threads with pigments from the contaminants and so on.

Accordingly, it has been essential to develop a method of producing pure and long bagworm silk threads comrising no contaminants, for practical application of bagworm silk threads as a novel material of biological origin.

CITATION LIST

Patent Literature

Patent Literature 1: WO2012/165477

Non-Patent Literature

Non-Patent Literature 1: Shigeyosi Ohsaki, 2002, Sen'i Gakkaishi (Sen'i To Kogyo), 58: 74-78.
Non-Patent Literature 2: Kuwana Y, et al., 2014, PLoS One, DOI: 10.1371/journal.pone.0105325
Non-Patent Literature 3: Gosline J. M., et al., 1999, 202, 3295-3303.

SUMMARY OF INVENTION

Technical Problem

An object of the present invention is to develop a method of producing a long bagworm silk thread comprising no contaminants, such as pieces of leaves and twigs, and a device for implementing the production method.

Solution to Problem

In the course of studying bagworm silk threads to solve the aforementioned problems, the present inventors found that bagworm silk threads include at least two types of silk threads, i.e., nest silk thread constituting the nest and foothold silk thread serving as a foothold for migration, and these silk threads differs in their mechanical properties. Foothold silk threads were thicker and stronger than nest silk threads. Foothold silk threads were also superior to silk threads from silkworm and threads from Araneus ventricosus in terms of values of elastic modulus, fracture strength, and toughness. Furthermore, it was found that foothold silk threads can be collected as pure bagworm silk threads without contaminants, such as pieces of leaves and twigs, differently from nest silk threads.

As described above, the foothold silk threads are usually spun in a zigzag pattern, and collection thereof was difficult. The studies of the present inventors led to the development of a method of making a bagworm spin foothold silk threads in a state nearly parallel to a rail by placing the bagworm on the rail having a specific width. Then, the present inventors succeeded in producing meter-scale continuous pure bagworm silk threads, which had hitherto been considered impossible, by implementing a method of spinning based on the aforementioned findings. The present invention has been completed on the basis of the findings and successful examples, and provides the following.

(1) A method of making a bagworm spin a long silk thread, the method comprising a process of making the bagworm having its nest hang its legs on a rail and continuously spin the thread along the rail, wherein the rail has a width smaller than the maximum width between the left and right legs when the bagworm used spreads out its legs and wherein the rail is such that the bagworm can hang its legs on the rail.
(2) The method according to (1), wherein the rail has a closed-ring structure or wherein the rail has an open-ring structure having one or more gaps which the bagworm can cross.
(3) The method according to (1) or (2), wherein the rail has an inclination of 0 to 70 degrees upward or 0 to 70 degrees downward.

(4) The method according to any one of (1) to (3), wherein the length of the continuously spun silk thread is 1 m or longer.

(5) A method of producing a long bagworm silk thread, the method comprising: a spinning process of making a bagworm having its nest hang its legs on a rail and continuously spin the thread along the rail, wherein the rail has a width smaller than the maximum width between the left and right legs when the bagworm used spreads out its legs and wherein the rail is such that the bagworm can hang its legs on the rail; and a collection process of collecting a long silk thread from the rail after the spinning process.

(6) The method according to (5), further comprising a scouring process of scouring the long silk thread simultaneously with or subsequently to the collection process.

(7) The method according to (5) or (6), further comprising a twisting process of twisting the silk threads after the collection process or the scouring step.

(8) The method according to any one of (5) to (7), wherein the rail has a closed-ring structure or wherein the rail has an open-ring structure having one or more gaps which the bagworm can cross.

(9) The method according to any one of (6) to (8), wherein the rail has an inclination of 0 to 70 degrees upward or 0 to 70 degrees downward.

(10) The method according to any one of (5) to (9), wherein the bagworm used is in the last instar.

(11) The method according to any one of (5) to (10), wherein the length of the continuously spun silk thread is 1 m or longer.

(12) A bagworm-derived silk thread having a continuous length of 1 m or longer.

(13) The silk thread according to (12), wherein the silk thread is a monofiber.

(14) A fabric comprising a silk thread produced by the method of producing a long bagworm silk threads according to any one of (5) to (11) or the silk thread according to (12) or (13).

(15) A device for producing a long bagworm silk thread, the device comprising: a rail having a width smaller than the maximum width between the left and right legs when the bagworm used spreads out its legs and wherein the rail is such that the bagworm can hang its legs on the rail.

(16) The production device according to (15), wherein the rail is composed of a material with a smooth surface.

(17) The production device according to (15) or (16), wherein the rail is composed of an edge part of a plate-shaped member.

(18) The production device according to any one of (15) to (17), wherein the rail has a closed-ring structure or wherein the rail has an open-ring structure having one or more gaps which the bagworm can cross.

(19) The production device according to any one of (15) to (18), wherein the rail has an inclination of 0 to 70 degrees upward or 0 to 70 degrees downward.

Advantageous Effects of Invention

By the method of making a bagworm spin a long silk thread according to the present invention, it is possible to make a bagworm spin a long foothold silk thread.

By the method of producing a long bagworm silk thread according to the present invention, a bagworm-derived pure and long foothold silk thread having a length of 1 m or longer can be produced.

By the device for producing a long bagworm silk thread according to the present invention, the method of producing a long bagworm silk thread can readily be carried out.

BRIEF DESCRIPTION OF DRAWINGS

FIG. 1A shows the appearance of a nest of a bagworm of *Eumeta japonica* (a *Eumeta japonica* bagworm). FIG. 1B shows the inside of the nest of a *Eumeta japonica* bagworm, which has been cut and opened along the longitudinal axis. The worm located in the middle is an *Eumeta japonica* larva, i.e., an *Eumeta japonica* bagworm.

FIG. 2A shows the spinning behavior of an *Eumeta japonica* bagworm during migration. FIG. 2A shows how a bagworm moves while spinning a foothold silk thread (arrowhead) and hooks its claws on the foothold silk thread spun by the bagworm (thin arrow), and how the nest is open at one end of the nest for exposing a part of its body during migration (thick arrow). FIG. 2B shows the state of foothold silk threads when a *Eumeta japonica* bagworm spins foothold silk threads under normal uncontrolled conditions. FIG. 2B shows how foothold silk threads spun in a zigzag pattern are entangled with each other in a complicated manner.

FIG. 3A shows a scanning electron micrograph of a spun fiber (a foothold silk thread) of an *Eumeta japonica* bagworm. FIG. 3B shows a schematic of a spun fiber in a bagworm silk thread. The fiber has a structure in which two flat-shaped monofibers (microfilaments) (301) are joined side-by-side by a gummy material (not shown) coating the monofibers.

FIG. 6 shows how a bagworm hangs its legs on a rail. FIG. 6A shows how a bagworm hangs its legs (arrowheads) on a rail (thin arrow) in a sandwich fashion. The shown picture was taken from right above the horizontal rail. The bagworm is moving in the direction indicated by the thick arrow, while hanging on the rail and hanging down therefrom. FIG. 6B shows how a bagworm hangs its legs (arrowheads) on a rail (thin arrow) as if the bagworm places its shoulder onto the rail. The shown picture was taken from diagonally above the horizontal rail. The bagworm is moving in the direction indicated by the thick arrow, while hanging on the rail and hanging down from a side surface of the rail.

FIG. 13A shows a bundle of bagworm silk threads after the collection process. FIG. 13B shows a bundle of bagworm silk threads after the scouring process. FIG. 13C shows a bagworm silk thread after the twisting process. FIG. 13D shows a fabric woven with bagworm silk threads after the twisting process.

DESCRIPTION OF EMBODIMENTS

Figure 4:
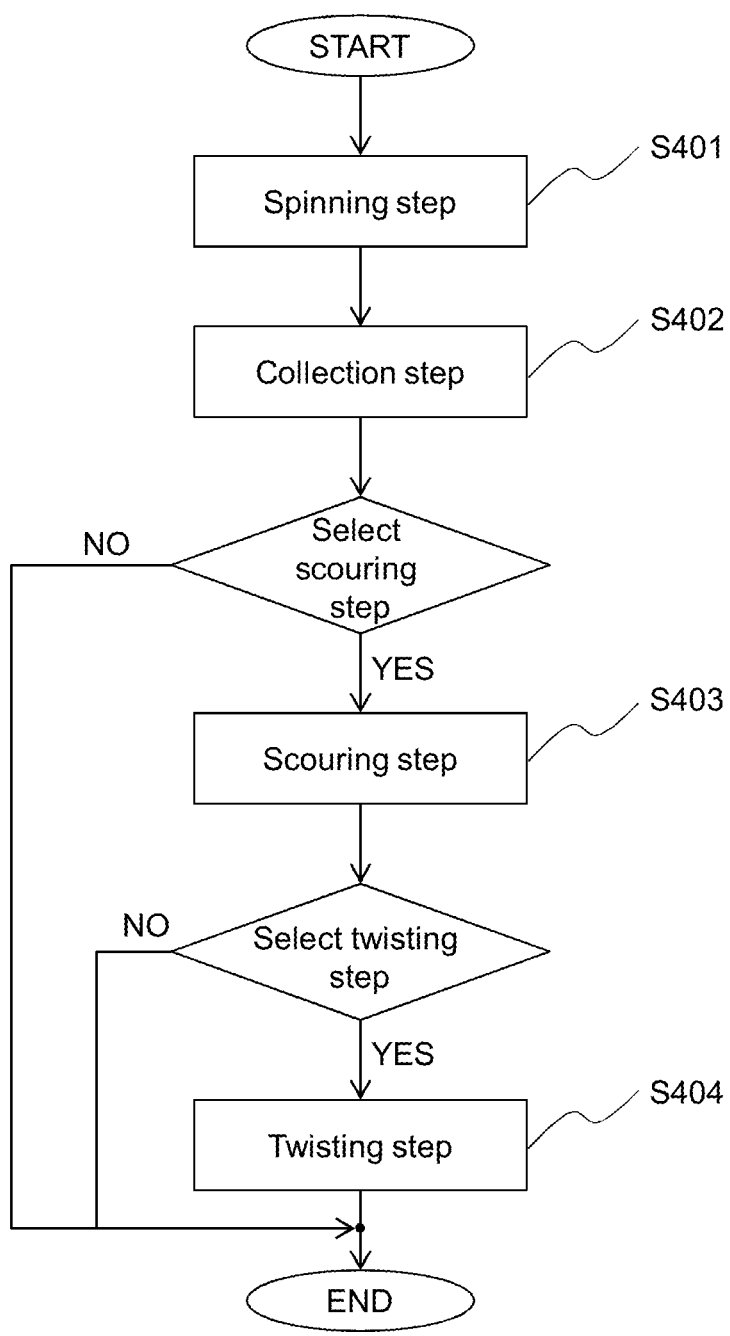
FIG. 4 shows a basic process flow diagram of a method for producing a long bagworm silk thread according to the present invention.

1. Method of Making a Bagworm Spin a Long Silk Thread
1-1. Overview

The first aspect of the present invention is a method of making a bagworm spin a long silk thread. The method of the present invention comprises a process of making a bagworm having its nest hang its legs on a rail and continuously spin a thread along the rail, wherein the rail has a specific width and wherein the rail is such that the bagworm can hang its legs on the rail. By the method of the present invention, it is possible to make a bagworm spontaneously spin meter-scale silk threads, which have hitherto been considered impossible.

1-2. Definition

The terms frequently used herein are defined as described below.

The term "bagworm" collectively refers to a moth larva belonging to the family Psychidae in the order Lepidoptera, as described above. Moths belonging to the family Psychidae are distributed worldwide and larvae (bagworms) of any species of the moths spend the whole larval stages living in nests covered with natural materials, such as pieces of leaves and twigs, which are assembled by silk threads spun by the larvae themselves. The nests are spindle-shaped, cylinder-shaped, or cone-shaped bag-like nests that can accommodate the whole body of a bagworm. Bagworms usually hide themselves inside the nests and always carry the nests even during eating and migration, and in principle, even pupate inside the nests.

The species, instar, and gender of bagworms used herein are not limited, provided that the bagworms are larvae of a moth species belonging to the family Psychidae and that the species makes a nest as described above. For example, the family Psychidae includes the genera *Acanthopsyche, Anatolopsyche, Bacotia, Bambalina, Canephora, Chalioides, Dahlica, Diplodoma, Eumeta, Eumasia, Kozhantshikovia, Mahasena, Nipponopsyche, Paranarychia, Proutia, Psyche, Pteroma, Siederia, Striglocyrbasia, Taleporia, Theriodopteryx, Trigonodoma*, etc., and bagworms used herein are a species belonging to any genus. Specific examples of Psychidae species include *Eumeta japonica, Eumeta minuscula,* and *Nipponopsyche fuscescens*. The instar of the larvae may be any instar between the first instar and the last instar. However, large bagworms are preferable for the purpose of obtaining thicker and longer bagworm silk threads. For example, among larvae of the same species, larvae in the last instar are more preferable, and female larvae are more preferable than male larvae because females grow larger than males. Additionally, among the family Psychidae, large species are more preferable. Thus, *Eumeta japonica* and *Eumeta minuscula* are species that are suitable as the bagworms used in the present invention.

The term "silk thread" as used herein refers to a proteinous thread from an insect, which is spun by the insect in larval or adult stage for the purpose of nest building, migration, anchoring, cocooning, prey capture, and the like. When the term "silk thread" is simply recited herein, it means bagworm silk thread, unless specifically noted.

The term "bagworm silk thread" as used herein refers to a bagworm-derived silk thread. The "bagworm silk thread" herein encompasses a monofiber, a spun fiber, and fiber assembly.

The term "monofiber" as used herein, which is also referred to as monofilament, is the smallest filament unit constituting fiber components. The monofiber contains a fibroin-like protein as a main component. Bagworm silk threads and silkworm silk threads in natural states are usually spun as a bifilament, but do not exist as a monofiber. However, monofibers can be obtained by removing gummy material in the scouring process in the second aspect described below.

The term "spun fiber" as used herein refers to an unprocessed silk thread just spun by bagworms, silkworms or the like, or just secreted by spiders. A spun fiber of bagworms is composed of a bifilament, which is a pair of monofibers, as shown in FIG. 3. This form is based on a structure in which two monofibers spun from the spinnerets located on each of the left and right sides of a bagworm are joined together by a sericin-like gummy material during spinning. When used in conjunction with the term "spin" in a phrase such as "a bagworm spun silk thread" or "spin a bagworm silk thread," the term "silk thread" is intended to mean a spun fiber in principle.

The term "fiber assembly" as used herein, which is also referred to as multifilament, refers to a fiber composed of a plurality of bundles of fibers. A fiber assembly refers to a so-called raw silk thread, and is in principle composed of a plurality of monofibers. Herein, however, a fiber assembly also includes those composed of a plurality of monofibers and spun fibers, or a plurality of spun fibers. The term "fiber assembly" as used herein can encompass a fiber mixture in which fibers other than bagworm silk threads such as silkworm silk threads and the like are mixed. However, the term is generally intended herein to mean a fiber assembly composed only of bagworm silk threads, unless specifically noted. A fiber assembly is twisted through the twisting process described in the second aspect below to become a stronger silk thread. Herein, the fiber assembly includes not only twisted fiber assemblies but also non-twisted fiber assemblies showing a soft and smooth texture.

Bagworm silk threads include foothold silk threads and nest silk threads, as described above. The "foothold silk thread" refers to a silk thread spun by a bagworm in advance of migration and functions as a foothold for preventing fall from a branch, leaf, or the like during migration. A bagworm usually uses the foothold silk thread as a foothold and hooks its claws onto the foothold silk thread to move in the direction of migration. A bagworm spins foothold silk threads in a zigzag pattern, which facilitates the bagworm to hang the left and right legs thereon and which also allows the silk thread attachment sites and the load on the silk thread to be distributed left and right. On the other hand, the "nest thread" refers to a silk thread forming a nest, which is spun to assemble pieces of leaves and twigs or to make an internal wall of a nest so that its accommodation space becomes a comfortable environment. In principle, foothold silk threads are thicker and also mechanically stronger than nest silk threads.

The term "long" refers to a length longer than the normal length in the art. Herein, the term "long" refers to being longer than the length of spun silk threads (a length of less than 1 m) obtainable from bagworms using conventional technology in particular. Specifically, the term "long" refers to 1 m or longer, or 1.5 m or longer, preferably 2 m or longer, more preferably 3 m or longer, 4 m or longer, 5 m or longer, 6 m or longer, 7 m or longer, 8 m or longer, 9 m or longer, or 10 m or longer. The upper limit of the length is not particularly limited, but corresponds to the length of silk threads that bagworms can continuously spin in the method of the present invention, including, for example, 1.5 km or shorter, 1 km or shorter, 900 m or shorter, 800 m or shorter, 700 m or shorter, 600 m or shorter, 500 m or shorter, 400 m or shorter, 300 m or shorter, 200 m or shorter, or 100 m or shorter. The length of a spun fiber of bagworm silk threads is also the length of a monofiber constituting it, and corresponds to the length of the thread continuously spun by a bagworm. Therefore, a longer bagworm silk thread can be obtained if it is possible to make a bagworm continuously spin a thread. Thus, the method of the present invention is also a method of making a bagworm continuously spin a silk thread.

1-3. Method

The method of the present invention comprises a spinning process as an essential process.

The "spinning process" is a process of making a bagworm having its nest hang its legs on a rail and continuously spin a thread along the rail under an active condition of the bagworm. The configuration of the rail is described in detail in the "device for producing a long bagworm silk thread" of the third aspect described below, and is thus not specifically described here.

The term "active condition" as used herein refers to a condition under which bagworms can perform activities involving usual movements such as migration and eating. Such conditions include, for example, temperature, atmospheric pressure, humidity, brightness, and oxygen level, and the most important condition in the present invention is temperature. Since insects are poikilotherms, they suspend activities and enter dormancy as the air temperature decreases. Thus, among the active conditions in the present invention, the lower limit of the suitable air temperature is a temperature at which bagworms do not enter dormancy. The specific temperature varies depending on the species, and may be generally 10° C. or higher, preferably 12° C. or higher, more preferably 13° C. or higher, further preferably 14° C. or higher, still more preferably 15° C. or higher. On the other hand, the upper limit of temperature is the upper limit of temperature under which bagworms can survive. In general, the temperature may be 40° C. or lower, preferably 35° C. or lower, more preferably 30° C. or lower, further preferably 27° C. or lower, still more preferably 25° C. or lower. The atmospheric pressure, humidity, brightness, oxygen concentration, and the like may be equal to or around, for example, those in plains in temperate areas. For example, the atmospheric pressure is around 1 atmosphere, the humidity ranges from 30 to 70%, and the brightness is 6 to 18 hours of bright condition out of 24 hours, and the concentration of oxygen in the atmosphere ranges from 15 to 25%.

The bagworm used in this process is a bagworm having its nest. Since bagworms generally behave with their nests, a bagworm including its nest may be used in this process. A bagworm removed from its nest becomes restless and cannot accomplish the object of the present invention, and therefore is not used. Additionally, the nest may not be intact, provided that the nest can hide almost the whole body of the bagworm. The nest is not necessarily composed of natural materials such as pieces of leaves and twigs and may be created using artificial materials (such as paper pieces, wood chips, fiber fragments, metal pieces, plastic pieces, and the like).

The term "hang on" generally refers to hooking and holding, but herein refers to that a bagworm hangs its legs on a rail to bear the weight of the bagworm itself (including the weight of the body and the nest) and to prevent falling from the rail. However, a bagworm may transiently hang its legs on a foothold silk thread spun by itself in the course of migration. A bagworm can freely hang on and release, and it does not mean that the temporarily hung legs are fixed at that position. The bagworm can freely move on a rail by repeating hanging on and release of its legs.

Figure 5:
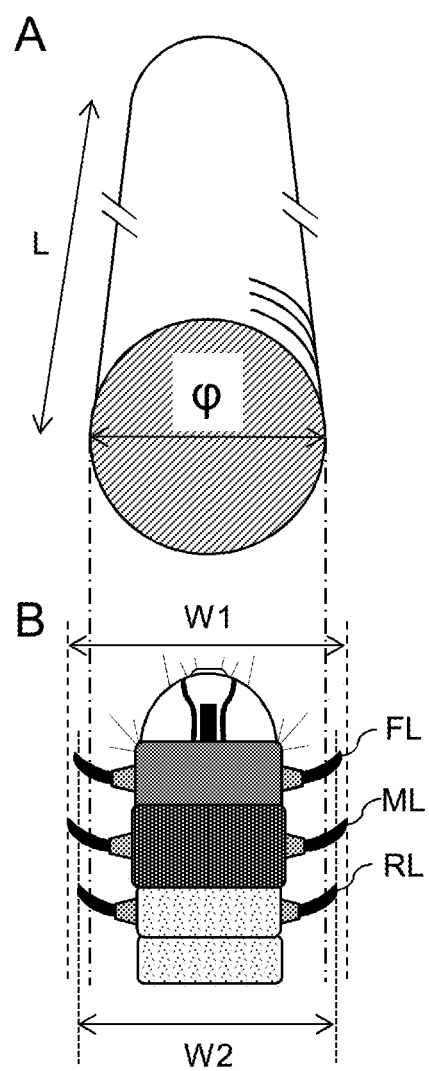
FIG. 5A shows a schematic of a rail according to the present invention. This figure shows a rail having a circular cross section. In the figure, L and φ respectively represent the length of the rail in the longitudinal axis and the cross-sectional diameter of the rail. In this rail, φ corresponds to the width of the rail.
FIG. 5B shows a dorsal view of the head and thorax of a bagworm spreading out the legs to the left and right at the maximum width. In the figure, FL, ML, and RL respectively represent front legs, middle legs, and rear legs. Also, W1 and W2 represent the maximum widths between the left and right legs when the bagworm spreads out its legs, for middle legs and posterior legs, respectively.

The term "leg" as used herein refers to an entire leg or a part of a leg of a bagworm. Legs called thoracic legs extend from the thorax of a bagworm, as shown in FIG. 5B. The thoracic legs consist of three legs (front, middle, and rear legs) unilaterally, which means three pairs of left and right legs, for a total of six legs. Any of the legs may be hung on a rail. Further, the number of legs hung on a rail may be any of 1 to 6, but is preferably at least two or more for moving on the rail. For example, the legs hung on a rail include any two or more legs out of three legs on either the left or right side, specifically front and middle legs, front and rear legs, middle and rear legs, and front, middle, and rear legs on the left side. Additionally, the legs hung on a rail include at least one or more legs on each of the left and right sides out of the six legs.

The phrase "make a bagworm hang its legs on a rail" as used herein refers to inducing a bagworm to spontaneously hang its legs on a rail, in principle. The phrase can include artificially making a bagworm hang its legs on a rail. However, even if one tries to force a bagworm to hang on a rail by an ordinary method with human hands, the bagworm become cautious, and it is not possible to successfully make a bagworm hang on a rail. The method of inducing a bagworm to hang on a rail is not particularly limited. Examples of the method include a method using a guidepath. The "guidepath" as used herein refers to a subsidiary walkway that is capable of inducing a bagworm to move spontaneously to the rail. The shape of the guidepath is not particularly limited, but examples of the guidepath include a single rail similar to a rail, or a plane like a wall. Examples of the method of guiding a bagworm to a rail using a guidepath include a method utilizing the nature of bagworms to move to a higher location. Specifically, once a bagworm is placed at a location lower than a rail and a guidepath is placed between the location where the bagworm is placed and the rail, the bagworm spontaneously goes up the guidepath and reaches the rail. After reaching the rail, the bagworm will automatically hang its legs on the rail due to the structure of the rail.

By making a bagworm hang on a rail under active conditions, the bagworm starts to continuously spin a thread while spontaneously moving along the rail. The phrase "continuously spin a thread" as used herein refers to spinning a thread without interruption. Once the silk thread spewed from the left and right spinnerets located on the mouth of a larva breaks, the continuity is lost.

The direction in which a bagworm moves on a rail can be controlled to some extent by the shape or inclination of the rail. For example, when the inclination of a rail is 0 degree, i.e. horizontal, a bagworm continues to move on the rail in the same direction as the direction in which the bagworm initially started moving. Specifically, once a bagworm hanging on a circular and horizontal rail starts moving in a clockwise direction, the bagworm keeps the clockwise direction in principle. On the other hand, bagworms have a nature to move to a higher location from the current position, as described above. Therefore, when a rail is not horizontal but is inclined, a bagworm moves along the rail towards the direction of a higher location by making the bagworm hang on at the lowest position of the rail. By utilizing these characteristics, it is possible to make a bagworm on a rail move in a desired direction.

As described above, a bagworm essentially spins a foothold thread in a zigzag pattern towards the direction of movement during migration. However, by the method of the present invention, a bagworm spins a foothold silk thread nearly in parallel with a rail. This is based on the structure of a rail and the nature of a bagworm. The rail used in the method of the present invention is such that a bagworm can hang its legs on the rail, and the rail has a specific width, which is described in detail in the third aspect. When a bagworm moves on a rail having such a structure, it is difficult for the bagworm to spin a foothold silk thread in a zigzag pattern, and the bagworm spins a thread nearly in parallel with the rail. The foothold silk thread spun in parallel cannot have strength sufficient to bear the weight of the bagworm itself and appropriate process size intervals. In this case, however, the bagworm can move by hanging its legs on the rail itself. Thus, it is thought that the foothold silk thread spun according to the method of the present invention is spun as an instinctive behavior associated with the migration behavior, without achieving the original function as a foothold for migration. The method of the present invention utilizes this feature.

The bagworm used in this process may be an individual collected in the field or an individual bred in successive generations under artificial conditions. In either case, an individual which is not starved is preferable, and an individual which is fed sufficient amount of food before use is more preferable. An individual which is not starved and is fed sufficient amount of food continues to move on a rail and spin a thread for a period from 1 hour to 4 days, from 3 hours to 3 days, or from 6 hours to 2 days, under the conditions described above. To make a bagworm continue to spin a thread, the structure of a rail is preferably a closed-ring structure having no terminal, i.e., having no end, or an open-ring structure having one or more gaps which the bagworm used can easily cross.

By the method of the present invention, foothold silk threads of bagworms having a continuous length of 1 m or longer can be obtained.

1-4. Effect

By the method of making a bagworm spin a long silk thread according to the present invention, it is possible to make a bagworm continuously spin a thread. This method allows for mass production of long bagworm silk threads at a practical application level, which are stronger foothold silk threads, although the production thereof has hitherto been considered impossible.

2. Method of Producing Long Bagworm Silk Threads 2-1. Overview

The second aspect of the present invention is a method of producing long bagworm silk threads. According to the production method of the present invention, which has conventionally been difficult, abundant production of long bagworm foothold silk threads can be easily and stably obtained. The production method of the present invention can be implemented, for example, using an apparatus for producing long bagworm silk thread of the third aspect.

2-2. Method

The flow of the production method of the present invention is shown in FIG. 4. The production method of the present invention comprises the spinning process (S401) and the collection process (S402) as essential processes. The method also comprises the scouring process (S403) and/or the twisting process (S404) as optional processes. Though FIG. 4 shows the basic flow consisting of the collection process (S402) followed by the scouring process (S403) and the subsequent twisting process (S404), the optional processes are not limited by the basic flow. For example, the scouring process (S403) and the collection process (S402) may be conducted simultaneously, as described below, or the twisting process (S404) may be conducted after the process (S402) and before the scouring process (S403). Each of the processes will be specifically described below.

(1) Spinning Process (S401)

The "spinning process" is a process that a bagworm with the nest thereof is made to continuously spin a thread along a rail under the active conditions, wherein the legs of the bagworm are held on the rail having a specific width and being capable of holding the legs of the bagworm used.

The details of this process follow those of the spinning process in the method of making a bagworm spin a long silk thread of the longer.

(2) Collection process (S402)

The "collection process" is a process of collecting long bagworm silk threads from a rail, from which a bagworm has been recovered or removed after the spinning process. In this process, foothold silk threads obtained from bagworms are spun fibers adhered to the rail by means of a sericin-like gummy material. A method of collecting bagworm silk threads is not limited to a particular method, provided that the bagworm silk threads are not torn during collection. For example, a scraper or the like can be used to physically release and collect bagworm silk threads from a rail. Particularly in cases where a rail has a smooth surface or a surface coated with a releasing agent in advance before the spinning process, the releasing operation is easily accomplished. By this method, bagworm silk spun fibers running nearly parallel to a rail can be collected.

Additionally, in cases where a rail has a rough surface or a very uneven surface, bagworm silk threads are strongly adhered to the rail by means of the sericin-like gummy material, which makes it difficult to release or collect the silk threads from the rail. In this case, this process and the scouring process as described below may be conducted simultaneously to prevent bagworm silk threads from being torn during collection. According to this procedure, bagworm silk threads can be easily collected from a rail because the gummy material is degraded and removed through the scouring process. Additionally, the bagworm silk threads can be obtained as monofibers without the gummy material, which are the same as those obtained after the scouring process, because the collection process and the scouring process are performed simultaneously. By this process, bagworm foothold silk threads having a length of 1 m or longer can be obtained, which have not hitherto been physically obtained.

(3) Scouring process (S403)

The "scouring process" is a process of scouring long silk threads. The term "scouring" refers to removing a sericin-like gummy material from spun silk threads (spun fibers) to obtain monofibers. This process is typically conducted after the above-described collection process, and may be conducted simultaneously with the collection process, as described above. Additionally, in cases where a twisting process follows the collection process, prior to this process, as described below, this process may be conducted after the twisting process. This process is an optional process and may be conducted as necessary.

A method of scouring bagworm silk threads is not limited to a particular method, provided that a gummy material can be removed without weakening the strength of the fiber components of the silk threads. For example, any scouring method for silkworm silk threads may be applied. Specifically, bagworm silk threads recovered in the collection process should be boiled in a sodium bicarbonate solution at a concentration of 0.01 mol/L to 0.1 mol/L, 0.03 to 0.08 mol/L, or 0.04 to 0.06 mol/L for a time period from 5 minutes to 1 hour, preferably 10 to 40 minutes, more preferably 15 to 30 minutes. By this process, monofibers from foothold silk threads having a length of 1 m or longer can be obtained.

(4) Twisting process (S404)

The "twisting process" is a process of twisting bagworm silk threads obtained after the collection process or the scouring process. The term "twisting" refers to winding threads together to produce a yarn. In this process, plural bagworm silk spun fibers and/or monofibers are twisted to produce bagworm silk yarns having toughness.

In the twisting process, monofibers from bagworm silk threads obtained after the scouring process may be gathered into bundles and then twisted, or alternatively bagworm silk spun fibers obtained after the collection process may be gathered into bundles and then twisted. In the former case, twisted bagworm silk yarns without a gummy material are obtained. In the latter case, twisted bagworm silk yarns consisting of spun fibers containing a gummy material are obtained. Thus, the obtained bagworm silk yarns may be used as bagworm silk yarns which have not undergone the scouring process and consequently contain a gummy substance, or may be scoured as necessary to produce twisted bagworm silk yarns without a gummy material.

In this process, bagworm silk fibers may be blended with other fibers, for example animal fibers such as silkworm silk fibers, plant fibers such as cotton fibers, synthetic fibers such as polyester fibers, or recycled fibers such as rayon, or the like, to form bundles of fibers and then to twist the resulting fiber bundles. In the production of one strand of twisted bagworm silk yarn, the number of constituent spun fibers and/or monofibers is not limited to a particular number. For example, the number ranges from 2 to 200, from 4 to 150, from 6 to 100, from 8 to 50, or from 10 to 30.

The twisting is not limited by a particular method. Any methods known in the art may be implemented. Examples of the method include right-laid (S-laid) and left-laid (Z-laid). The twist number may be determined as appropriate. Plural strands of twisted bagworm silk yarn may be further twisted together by the process called plying to produce a thicker bagworm silk yarn. The twisting operation may be performed by hand or by using a yarn twister.

Long bagworm silk threads, which are obtained by the production method of the present invention, can be spun together into longer bagworm silk yarns.

2-3. Effect

Long bagworm silk threads having a length of 1 m or longer as monofibers or fiber assemblies, which has hitherto been considered impossible to produce, can be produced through the above-described processes. Therefore, fabrics comprising bagworm foothold silk threads, which has hitherto been impossible to produce, can also be produced using the long bagworm silk threads according to the present invention as a sole material or in combination with other fibers. Fabrics made of bagworm silk threads are beautiful and smooth, and have excellent tensile strength. Thus, long bagworm silk threads are promising not only as a material for clothes but also as a special material for, for example, medical materials and protective clothes, as in the case of spider thread. Long bagworm silk threads can further be used for quality fabric products (for example, quality legless chairs, sofas, curtains, fabric wallpapers, and the like, to which strong friction force is often applied).

According to the method of producing long bagworm silk thread of the present invention, pure and long bagworm-derived foothold silk threads having a length of 1 m or longer, which contain no contaminants, such as pieces of leaves and twigs, can be churned out.

3. Apparatus for Producing Long Bagworm Silk Thread 3-1. Overview

The third aspect of the present invention is an apparatus for producing long bagworm silk thread. The production apparatus of the present invention is characterized by comprising, as an essential component, a rail having a specific width and being capable of holding the legs of a bagworm. Long foothold silk threads can be easily obtained from bagworms with the production apparatus of the present invention.

3-2. Configuration

The production apparatus of the present invention comprises a rail as an essential component. The rail will be described below.

The term "rail" as used herein refers to a path with a linear structure on which a bagworm moves. The "linear structure" as used herein refers to a single-rail structure having a same or substantially same width, whose cross-sectional shape is not limited to a particular shape but includes circular shapes, approximately circular shapes (including oval shapes), polygonal shapes (including square and approximately square shapes), and combinations thereof.

The length of the rail is not limited. Because a bagworm spins a foothold silk thread in the direction along a rail, a longer rail can be used to obtain a longer foothold silk thread in principle. However, the method according to the first aspect of the present invention can collect foothold silk threads which have been spun so as to overlap each other on a rail, so that a foothold silk thread having a length longer than that of the rail can also be obtained when a bagworm repeatedly travels along the rail. For example, the rail should have a closed-ring structure or an open-ring structure with a gap(s) which a bagworm used can cross. In this case, a bagworm moves around the circular rail, and thereby a long silk thread can be obtained even if the rail has only a limited length. In this respect, the "closed-ring structure" or the "open-ring structure" has any of circular, approximately circular, square shapes, approximately square, and polygonal shapes, or a combination thereof.

Herein, the rail is not merely a supporting member on which a bagworm holds its legs to bear its own weight, but also the structure and width of the rail are important to achieve the object of the production apparatus of the present invention. That is, a rail in the production apparatus of the present invention is configured to meet the following three conditions.

The first condition is related to the linear structure. When a path on which a bagworm moves has a linear structure, the moving freely in the lateral direction of a bagworm is restricted, and thereby the bagworm only allows to move in the direction along the rail in principle. The movement of a bagworm can be controlled to some extent by the structure of the rail.

The second condition is that the width of a rail is less than the maximum width between the extended legs of a bagworm used to the production apparatus of the present invention.

The "width of a rail" as used herein refers to the length of a moiety of directly involved in holding legs. This length generally corresponds to the transverse (short axis) length of the rail. The maximum width of a rail is less than the maximum width between the extended legs of a bagworm used to the production apparatus of the present invention. In contrast, the minimum width of a rail is not limited to a particular length, as long as a bagworm can hold the legs on the rail. For example, the rail may be on the edge of a thin metal plate with a thickness of around 0.5 mm. In the rail shown in FIG. 5A, the cross-sectional diameter (φ) corresponds to the width of the rail.

The "maximum width between the extended legs of a bagworm" as used herein corresponds to the width (W1 or W2) between the left and right legs of the bagworm, which are extended as much as possible, as shown in FIG. 5B. A bagworm has three pairs of left and right legs (front legs, middle legs, and rear legs), and the maximum width between the extended legs preferably represents either of those except for the longest (maximum) width between the extended legs, namely the second longest width or the shortest width between the extended legs, more preferably represents the shortest (minimum) width between the extended legs. In FIG. 5B, the maximum width between the extended middle legs (ML), W1, is the longest among the three pairs of legs and the maximum width between the extended posterior legs, W2, is the shortest among the three pairs of legs. Therefore, when the width of a rail is determined, the maximum width between the extended front legs or between the extended rear legs, particularly the maximum width between the extended posterior legs, W2 is preferable as the maximum width between the extended legs of a bagworm. The maximum width between extended legs varies depending on the species, male and female, and instar of larvae, but generally falls within a specific range if the bagworms are the same species of nearly the same instar. For example, in *Eumeta japonica,* the maximum width between extended legs of young instar larva (around the first to third instar) ranges from 2 mm to 4 mm or from 3 mm to 5 mm. That of the middle instar larva (around the fourth to fifth instar) ranges from 3 mm to 7 mm or from 4 mm to 8 mm. That of the penultimate instar larva or last instar larva ranges from 4 mm to 9 mm, from 5 mm to 10 mm, or from 6 mm to 12 mm. In *Eumeta minuscula,* the maximum width between extended legs of young instar larva (around the first to third instar) ranges from 1.5 mm to 3.5 mm. That of the middle instar larva (around the fourth to fifth instar) ranges from 2.5 mm to 6 mm or from 3 mm to 7 mm. That of the penultimate instar larva or last instar larva ranges from 3.5 mm to 8 mm, from 4 mm to 9 mm, or from 5 mm to 10 mm. Thus, the width of a rail should be changed as appropriate according to the species, instar, and male and female of bagworms used. In each larval instar, the width of a rail is preferably less than the shortest (minimum) among the maximum widths between the extended legs of bagworms of the species used, in terms of holding legs as described below.

Additionally, the third condition is that a bagworm can hold its legs on a rail.

Specific examples of the manner in which a bagworm "holds its legs on a rail" include a manner in which the bagworm holds the rail with at least a pair of legs, one each from the left and right sides, among the three pairs of legs, for a total of six legs. For example, FIG. 6A shows a picture taken from above a rail (arrow) made of a metal wire. In FIG. 6A, a bagworm moves in the direction indicated by the thick arrow by holding the rail between the six legs (arrowheads) from underneath. In this case, the bagworm is hung down from the rail. In this specification, the rail floor is directed downward when a bagworm hangs down from the rail as shown in the picture. In FIG. 6A, the rail floor is a surface facing the venter of the bagworm, which is out of sight in the picture.

Additionally, a manner in which a bagworm hooks the legs on either the left or right side on a rail from above is given as another example. For example, FIG. 6B shows a picture taken diagonally above a rail (arrow) located on the edge of a metal plate. In FIG. 6B, a bagworm moves in the direction indicated by the thick arrow by hooking the three right legs (arrowheads) onto the rail. In this case, a bagworm hangs down from a side surface of the rail by hooking the legs on the rail. Herein, the rail floor is directed upward when a bagworm hangs down from a side surface of the rail, as shown in the picture. In FIG. 6B, the rail floor is a surface on which the legs of a bagworm are hung.

Figure 7:
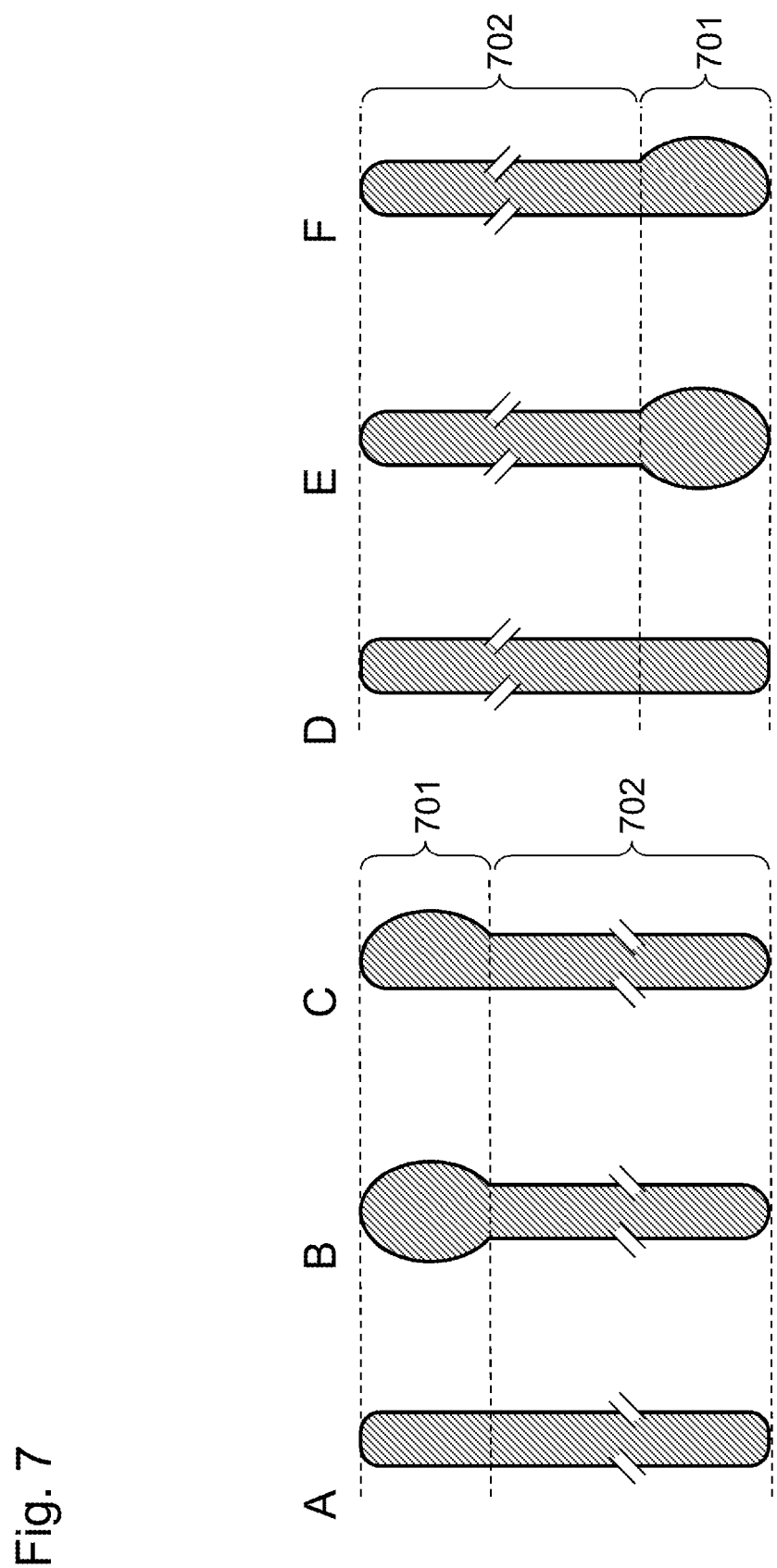
FIG. 7 shows drawings for describing rails that a bagworm can hang on. A to F show cross sections of a plate-shaped member (702) and a rail positioned at an edge part thereof (701). A to C show aspects in which the rail faces upward, and D to F show aspects in which the rail faces downward.

Any rail which fails to hold a bagworm is considered as not meeting the requirements for the rail of the present invention, even if the rail has a width less than the maximum width between the extended legs of the bagworm used to the production apparatus of the present invention. For example, in cases where the edge of a plate member made from a material with a smooth surface is configured into a rail, A to F shown in FIG. 7 are illustrated as the example. As a prerequisite, the width of a rail according to any of A to F shall be less than the maximum width between the extended legs of a bagworm. Among those, each of A to C shows a rail floor directed upward. In A, no bump is formed between the plate member and the edge (rail: 701); in B, the thickness of the rail is increased relative to that of the plate member on both sides to form an expanded portion; and in C, the thickness of the rail is increased relative to that of the plate member on only one side to form an expanded portion. In any configuration, a bagworm can hang on the rail. In contrast, each of D to F shows a rail floor directed downward. The rails according to D to F have similar structures according to A to C, respectively. Among those, each of E and F includes an expanded portion formed on a rail, which assists a bagworm to hang on to the rail, and D includes no bump functioning as a foothold on a rail, which no longer allows a bagworm to hang on the rail. Thus, any configuration as shown by D does not meet the requirements for the rail that is capable of holding the legs of a bagworm.

The material of the rail is not limited. For example, metals, ceramics (including enamel), glass, stones, resins (including synthetic and natural resins), wood materials (including branch, vine, bamboo, and the like), fibers, bones and fangs, and combinations thereof can be used. The material preferably has a sufficient strength to be invulnerable to biting attack of bagworms. For example, metals, ceramics, glass, stones, and the like are suitable. Additionally, a portion of a rail to which bagworm silk threads are adhered is preferably made from a material with a smooth surface to facilitate collection of bagworm spun silk threads. The "material with a smooth surface" as used herein refers to a material processable to form a smooth surface, such as metals, glass, and plastics. Additionally, any material coated with a paint or the like to obtain a smooth surface is included in the material with a smooth surface, even if the original material is difficult to polish for the formation of a smooth surface, such as wood materials and fibers.

The form of a member including a rail (a rail member) is not limited. For example, the rail member may have a wire-like or string-like structure like a metal wire which per se forms a rail, or may have a plate structure. In cases where the rail member is a plate member, a rail is included on the edge of the plate member. In this respect, the plate member and the edge may be made from an identical material or from different materials.

Figure 8:
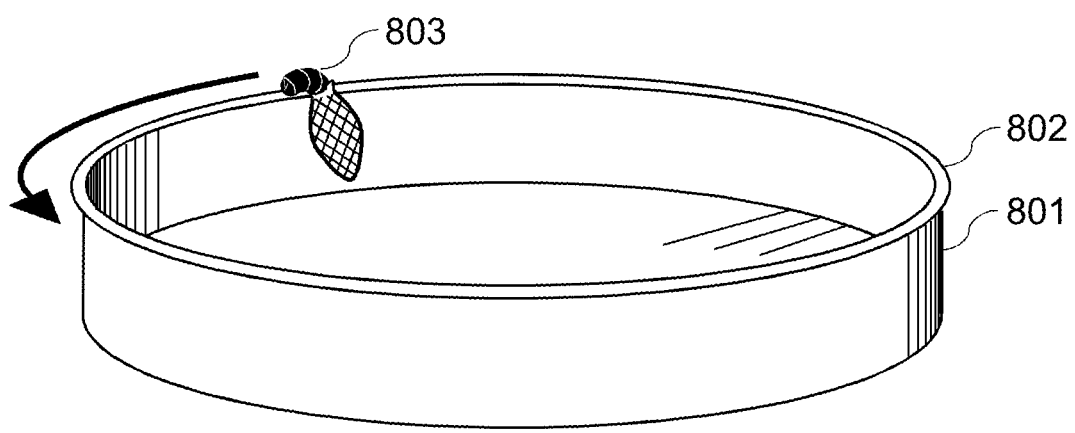
FIG. 8 shows an embodiment of a device for producing a long bagworm silk thread according to the present invention. This figure shows a device for producing a long bagworm silk thread having a closed-ring rail as an edge part (802) of a plate-shaped member (801).
Figure 9:
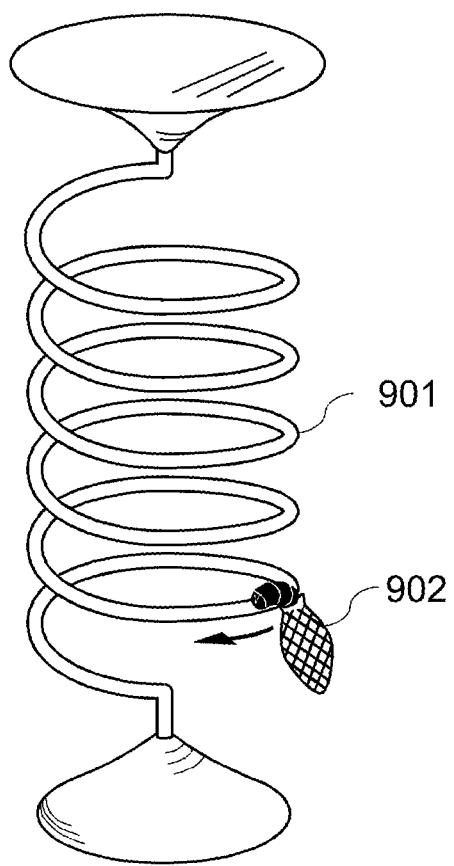
FIG. 9 shows an embodiment of a device for producing a long bagworm silk thread according to the present invention. This figure shows a device for producing a long bagworm silk thread wherein the rail (901) is composed of a helical wire member.
Figure 10:
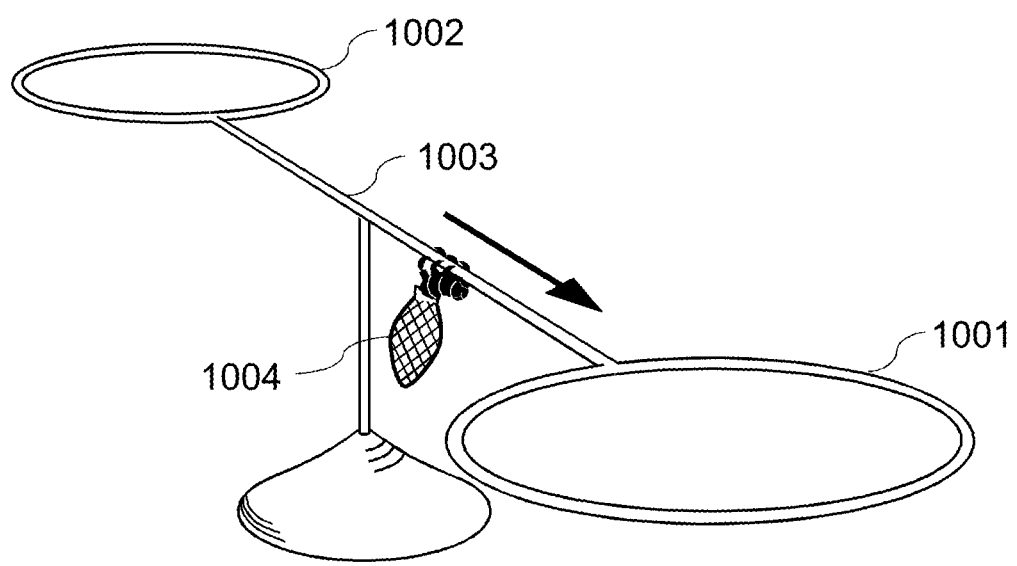
FIG. 10 shows an embodiment of a device for producing a long bagworm silk thread according to the present invention. This figure shows a device for producing a long bagworm silk thread wherein two closed-ring rails composed of a wire member (1001, 1002) are connected by a single rail (1003).

Embodiments of the rail will be described by illustrative examples shown in FIGS. 8 to 10. FIG. 8 depicts an example of the rail configured as the edge of a plate member (801). The rail (802) in this drawing has a closed-ring structure with the rail floor directed upward. A bagworm (803) placed on the rail in this production apparatus principally continues to move in the direction indicated by the arrow. FIG. 9 depicts an example of the rail which is made of a wire member such as a metal wire. The rail (901) in this drawing has a helical structure. Because bagworms have a tendency to move to a higher location, a bagworm (902) placed on the lower end of the rail in this apparatus moves upward, while spinning a thread. Once the bagworm reaches the upper end of the helical rail, the apparatus is turned upside down and the bagworm is again positioned at the lower end of the wire member, which allows the bagworm to continue continuous spinning. Additionally, FIG. 10 depicts an example of the rail which comprises a combination of circular rails and a linear rail. In FIG. 10, two closed ring-like rails (1001, 1002) are connected to one linear rail (1003), wherein those rails are made of a wire member such as a metal wire. A bagworm (1004) continue to move in the direction indicated by the arrow and then to return on the linear rail and/or move around the circular rail in the apparatus.

Figure 11:
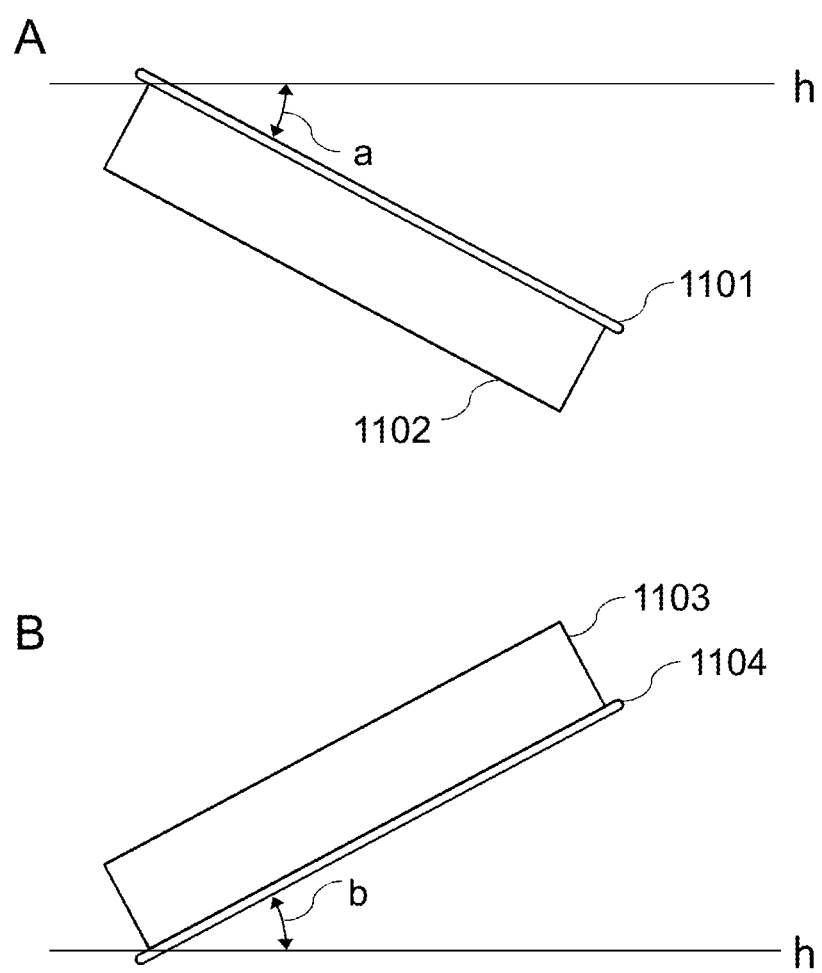
FIG. 11 shows drawings for describing the inclination of a rail in a device for producing a long bagworm silk thread according to the present invention. This figure shows the inclination (a and b) of the rail (1101, 1104) to the horizontal plane (h) in a case in which the rail faces upward (A) and in a case in which the rail faces downward (B), respectively, in the example of the device for producing a long bagworm silk thread comprising the plate-shaped member (1102, 1103) shown in FIG. 8.

The rail in the production apparatus of the present invention may have a slope. The slope relative to the horizontal surface preferably ranges from 0 to 70 degrees or from 0 to 50 degrees upward, or ranges from 0 to 70 degrees or from 0 to 50 degrees downward. The term "upward" or "downward" refers to the angle of the rail floor. For example, in cases where the production apparatus of the present invention comprises a rail on the edge of a plate member, as shown in FIG. 11, and the rail floor is directed upward, as shown in FIG. 11A, the inclination angle (a) between the horizontal surface and the rail floor should range from 0 to 70 degrees. Additionally, in cases where the rail floor is directed downward, as shown in FIG. 11B, the inclination angle (b) between the horizontal surface and the rail floor should range from 0 to 70 degrees.

3-3. Effect

According to the production apparatus for long bagworm silk thread, the method for producing long bagworm silk thread according to the present invention can readily be implemented, and the production of long bagworm foothold silk threads having a length of 1 m or longer can easily be obtained by using the production apparatus, which has hitherto been impossible.

EXAMPLES

Example 1: Production of Long Bagworm Silk Threads (Purpose)

Bagworm foothold silk threads are produced by the method according to the present invention for producing long bagworm silk thread.

(Method)

As the bagworm, the last instar larvae of *Eumeta japonica* collected at an orchard in Tsukuba, Ibaraki, Japan t were used (n=50). A production apparatus according to the present invention for long bagworm silk thread was used to produce long bagworm silk threads. An approximately square metal can was used as the production apparatus. In the metal can, a closed ring-like rail with its floor directed upward, which has a width of 1.7 mm and a perimeter of 1.1 m, is on the upper edge of the plate member corresponding to the side surface of the metal can. One bagworm was placed on the inner bottom surface of the metal can. After observing the state that the bagworm was reached the rail and move around the rail with spinning of threads, the bagworm was left on the rail directly for two days (i.e., the spinning process). Two days later, the bagworm was recovered or removed from the apparatus and bagworm silk threads (foothold silk threads) overlapped with each other on the rail were removed by using a scraper to collect an approximately square ring-shaped a bundle of bagworm silk threads (silk bundle) (i.e., the collection process). The total length of the spun foothold silk threads was calculated from the number of spun fibers constituting the obtained silk bundle and the perimeter of the rail. Then, any gummy material adhered to bagworm silk threads was scoured. In the scouring conditions, the bagworm silk threads were boiled in a 0.05 mol/L aqueous solution of sodium carbonate for 15 minutes, and further boiled for another 15 minutes after the aqueous sodium carbonate solution was replaced with fresh aqueous solution (i.e., the scouring process). After the scouring process for a total of 30 minutes, the bagworm silk threads were thoroughly washed with pure water and then dried in air. The 150 or more bagworm silk threads (monofibers) obtained after the scouring process were twisted by hand into bagworm silk yarns (i.e., the twisting process). The bagworm silk yarns were used in warp and weft to weave a fabric made of bagworm silk. (Result)

The bagworm, which had been placed on the inner bottom surface of the container, then spontaneously climbed to the wall until the bagworm reached the closed ring-like rail located on the top of the wall, and subsequently continued to move in the same direction around the rail with continuous spinning of threads. The time required for the bagworm to move once around the 1.1 m rail with spinning of threads was from about 5 minutes 30 seconds to about 7 minutes 30 seconds. This result indicated that the last instar larvae of *Eumeta japonica* can spin a thread at around a rate of 150 to 200 mm/min (1100 mm/7.5 min to 1100 mm/5.5 min), which is equal to about half the spinning rate of silkworms (300 to 400 mm/min; Kei-ichi Komatsu, 1997, "Invitation to Silk", Sciencehouse Inc., p20).

Figure 12:
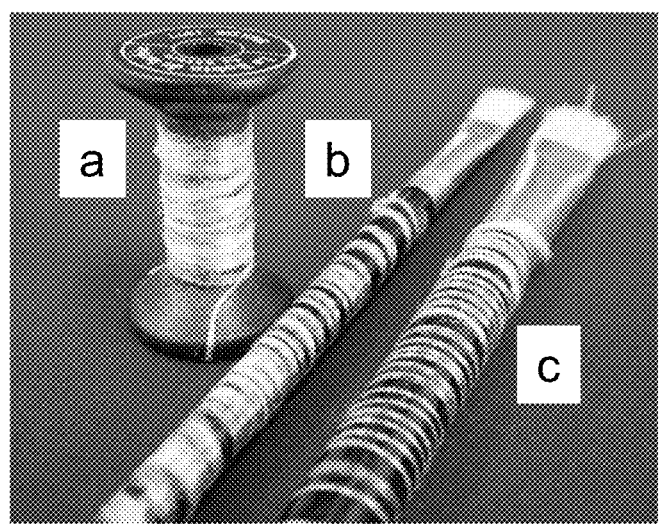
FIG. 12 shows bundles of bagworm silk threads obtained after the collection process, which are wound around a bobbin (a) or handles of paint brushes (b and c) in the method of producing a long bagworm silk thread according to the present invention. Pure and shiny long silk threads without contaminants were successfully obtained.

FIG. 12 shows bundles of bagworm silk threads obtained after the collection process and wound around a bobbin (a) or handles of paint brushes (b and c). Though it was difficult to collect spun fibers of nest silk threads even as short as 50 cm in accordance with conventional techniques, the method according to the present invention for producing long bagworm silk thread allowed bagworms to produce longer foothold silk threads.

Figure 13:
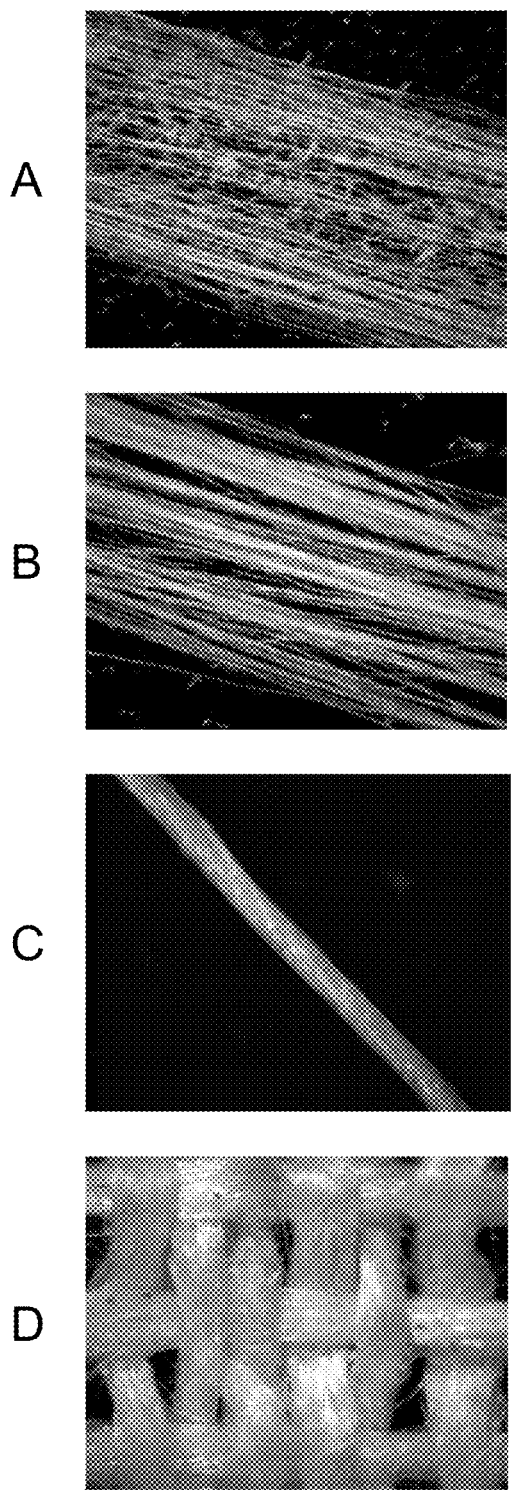
FIG. 13 shows magnified views of bagworm silk threads after each process in the method of producing a long bagworm silk thread according to the present invention and a fabric made of bagworm silk threads.

FIG. 13A depicts a view under a stereoscopic microscope of a bundle of bagworm silk threads obtained after the collection process. The bagworm foothold silk threads in this view were observed to run nearly parallel in the same direction and not to complicatedly tangle with each other. Additionally, the silk bundle in the view is a bundle of silk threads released and collected from the rail after the collection process. It was difficult to count the exact number of spun fibers in the silk bundle. However, the silk bundle was estimated to consist of at least 150 spun fibers. This result indicates that the bagworm moved at least 150 times around the closed ring-like rail with spinning of threads, which means that bagworm foothold silk threads with a length of at least 165 m (1.1m×150) or longer in total were produced by the method according to the present invention for producing long bagworm silk thread because the rail was 1.1 m long in total. Considering the fact that it was almost impossible to stably obtain bagworm silk threads with 1 m or longer in accordance with conventional techniques, this result has demonstrated a significant effect of the method according to the present invention for long bagworm silk thread production. Much longer bagworm silk threads can be obtained by making bagworms spin threads for a longer period of time under optimized conditions.

Additionally, the bagworm silk threads obtained in this procedure are foothold silk threads collected from a rail made of a metal and therefore are pure bagworm silk threads completely without any pieces of leaves and twigs. The bagworm silk threads obtained in this procedure are slightly fuzzy because a sericin-like gummy material remains on the silk.

FIG. 13B depicts a view under a stereoscopic microscope of a bundle of bagworm silk threads obtained after the scouring process. It was observed that the gummy material and fuzz were completely removed by the scouring process, and thereby the bagworm silk became only monofibers.

FIG. 13C depicts a view of a bagworm silk yarn obtained after the twisting process. It was observed that bagworm silk yarns as shiny and tough as ordinary silkworm silk yarns were obtained by the twisting process.

FIG. 13D depicts an enlarged view of a woven fabric produced by weaving the twisted bagworm silk yarns. It was demonstrated that the method according to the present invention for producing long bagworm silk thread enables production of a woven fabric using bagworm silk yarns, which has hitherto been impossible.

Example 2: Examination of Continuous Spinning Behavior of Bagworms (Purpose)

Bagworms have a tendency to spin foothold silk threads at least during migration. Accordingly, a bagworm continuously spins a thread as long as the bagworm continues to move on a rail, which also corresponds to the length of bagworm silk monofibers obtained by the present invention. Thus, the inventors examined how many hours bagworms can continue to spin on the apparatus according to the present invention for producing long bagworm silk thread.

(Method)

As the bagworm, the last instar larvae of *Eumeta minuscula* collected from trees planted in the grounds of National Agriculture and Food Research Organization, Japan were used (n=8). A stainless dish having a diameter ($\varphi$) of 75 mm and comprising a closed ring-like rail, which has a width of 0.85 mm and a perimeter of 235 mm, was used as the production apparatus. After one bagworm was placed on the bottom surface of the stainless dish, the time required for the bagworm to move from the start point to the end point of the rail was measured.

(Result)

The measured time of continuous spinning and length of spun fiber are presented in Table 1.

TABLE 1

| | 1 | 2 | 3 | 4 | 5 | 6 | 7 | 8 | Average |
|---|---|---|---|---|---|---|---|---|---|
| Time of continuous spinning (hr) | 51 | 51 | 50 | 48 | 48 | 38 | 34 | 34 | 44.25 |
| Length of spun fiber (m) | 459 | 459 | 450 | 432 | 432 | 342 | 306 | 306 | 398.25 |

It was found that the *Eumeta minuscula* continued to spin foothold silk threads while moving on the rail for 34 to 51 hours without interruption. That is, it was indicated that the use of the apparatus according to the present invention for producing long bagworm silk thread allows the bagworms to continuously spin threads from about 1.5 days to about two days without needing any special conditions or operations and also without eating or resting.

After the spinning process, a bundle of silk threads running nearly parallel to the rail was collected from the rail, similarly to Example 1. The total length of bagworm silk threads was calculated to be from 306 m to 459 m, based on the perimeter of the rail in the production apparatus.

From the time required to move once around the rail on the stainless dish, it was indicated that the last instar larvae of *Eumeta minuscula* can spin threads at almost the same rate as the last instar larvae of *Eumeta japonica*.

Example 3: Examination of Mechanical Properties of Bagworm Silk Threads (Purpose)

The mechanical properties of bagworm silk threads were examined.

(Method)

Spun fibers (bifilaments) obtained before scouring were used as the bagworm silk threads. A portion of the spun fibers obtained after the collection process in Example 1 were used as foothold silk threads (n=9). Additionally, silk threads collected from the innermost layers of nests for the last instar larvae of *Eumeta japonica* were used as nest silk threads (n=5). After dissecting the *Eumeta japonica* nests, the samples having a length of about 30 mm from the surface of the innermost layers were manually collected.

A tensile test was performed on each type of bagworm silk threads to evaluate four different mechanical properties: initial elastic modulus, fracture strength, elongation at break, and toughness. The initial elastic modulus refers to a value given as the initial slope of a stress-strain curve, which corresponds to the proportional constant in the deformation area meeting Hooke's law, which is the proportional relationship between stress and strain when a sample is pulled. In general, a higher value of the initial elastic modulus means a smaller strain for a given tensile stress, meaning more stiffness. Additionally, the fracture strength refers to the maximum stress applied to a thread just before the thread breaks. In general, a higher value of the ultimate tensile strength means a higher degree of resistance to stress. Furthermore, the elongation at break refers to the increased length of a thread at its break point. In general, a higher value of the elongation at break means a higher elasticity. Moreover, the toughness refers to the amount of work (energy) required to fracture a thread, which is given as the area under the stress-strain curve. In general, a higher value of the toughness means a higher degree of resistance to fracture.

The measurements were performed using a load cell of 5 N on a tensile tester (EZ Test; Shimadzu Co.) under the following measurement conditions: gauge length (the initial length of a sample), 13 mm; tensile speed, 10 mm/min; measurement environment, room temperature (25° C.) and 30% of humidity.

To evaluate the above-described four properties, a stress-strain curve was prepared by converting each measured value in the tensile test to a stress value obtained by dividing measured value by the cross-sectional area of each monofiber in the bagworm silk threads. The cross-sectional area of a monofiber was calculated as follows. When foothold and nest silk threads spun by a bagworm are observed under a scanning electron microscope (SEM), either of them shows a structure consisting of two flattened monofibers (monofilaments), as shown in FIG. 3, joined side-by-side along the longitudinal axis of each fiber by a gummy material. As shown in FIG. 3B, the cross section of a monofiber has an elliptical shape. When the ratio (a/b) between the major axis (a) and minor axis (b) of the ellipse was calculated, the ratio was led to the following value in either case of the foothold and nest silk threads: a/b=1.67±0.12 (n=15). The elliptical major axis (a) of two monofibers constituting the bagworm silk thread were measured used a light microscope (BZ-X700; KEYENCE Co.) for each sample used, and the cross-sectional area of each monofiber was calculated according to the elliptical area formula (A=$\pi$ab), based on the assumption that each monofiber has a cross section with the ratio a/b=1.67.

(Result)

The calculated values of the mechanical properties are presented in Table 2. In this table, the values of the same mechanical properties of bagworm silk threads from *Eumeta minuscula*, silkworm silk threads from Bombyx mori, and spider threads from Araneus ventricosus are shown as controls, which are cited from references. The methods to calculate the mechanical properties of the controls are the same as those for the mechanical properties of the present embodiment.

TABLE 2

|  |  | Elastic modulus (GPa) | Fracture strength (GPa) | Elongation at break (%) | Toughness (MJ/m$^3$) |
|---|---|---|---|---|---|
| *Eumeta japonica* | Foothold silk thread | 33.04 (±3.52) | 2.02 (±0.33) | 24.67 (±4.41) | 282.23 (±49.90) |
|  | Nest silk thread | 18.17 (±4.53) | 1.46 (±0.19) | 27.40 (±3.23) | 238.27 (±28.12) |
|  | Silk thread average | 27.09 (±3.21) | 1.80 (±0.22) | 25.76 (±2.88) | 264.64 (±31.86) |
| *Eumeta minuscula* [1] |  | 25 | — | — | — |
| *Bombyx mori* [2] |  | 7 | 0.6 | 18 | 70 |
| *Araneus ventricosus* [2] |  | 10 | 1.1 | 27 | 160 |

(References)
[1] Shigeyosi Ohsaki, 2002, Sen'i Gakkaishi (Sen'i To Kogyo), 58: 74-78.
[2] Gosline J. M., et al., 1999, 202, 3295-3303.

It was found that bagworm silk threads from *Eumeta japonica* included at least two types of silk threads, namely foothold and nest silk threads, showing different mechanical properties, as shown in Table 1. Additionally, it was found that the values of mechanical properties including initial elastic modulus, fracture strength, and toughness were higher in the foothold silk threads than in the nest silk threads.

In contrast, bagworm silk threads, particularly foothold silk threads, from *Eumeta japonica* had quite excellent mechanical properties, compared with silkworm silk threads from Bombyx mori and spider threads from Araneus ventricosus. For example, the elastic modulus of the foothold silk threads from *Eumeta japonica* bagworms was about 5 times higher than that of the silkworm silk threads and 3 times or more higher than that of the spider threads; the fracture strength of the foothold silk threads was 3 times or more higher than that of the silkworm silk threads and about 2 times higher than that of the spider threads; and the toughness of the foothold silk threads was 4 times or more higher than that of the silkworm silk threads and 1.7 times or more higher than that of the spider threads. Additionally, the elongation at break of the foothold silk threads was 1.3 times or more higher than that of the silkworm silk threads and was nearly equal to that of the spider threads.

All publications, patents, and patent applications cited herein should be incorporated herein by reference in their entirety.

The invention claimed is:

1. A method of producing a long bagworm silk thread, the method comprising:
   a spinning process of making a bagworm that carries a nest holding a rail with its legs under active conditions, and continuously spinning a thread while moving along the rail,
   wherein the rail has a width smaller than a maximum width between left and right legs of the bagworm when the bagworm spreads out its legs and wherein the rail is such that the bagworm can hang its legs on the continuous length of the rail;
   a collection process of collecting a long silk thread from the rail after the spinning process; and
   a scouring process of scouring the long silk thread simultaneously with or subsequently to the collection process,
   wherein a length of the continuously spun silk thread is 1 meter or longer.

2. The method according to claim 1, further comprising a twisting process of twisting the silk thread after the collection process or after the scouring process.

3. The method according to claim 1, wherein the rail has a closed-ring structure or wherein the rail has an open-ring structure having one or more gaps which the bagworm can cross.

4. The method according to claim 1, wherein the rail has an inclination of 0 to 70 degrees upward or 0 to 70 degrees downward.

5. The method according to claim 1, wherein the bagworm used is in a last instar.

6. The method according to claim 1, wherein the maximum width between the left and right legs of the bagworm is from 4 mm to 12 mm or from 3.5 mm to 10 mm when the bagworm is in a penultimate instar larva or a last instar larva.

* * * * *